United States Patent
Johansson et al.

(10) Patent No.: US 11,019,918 B2
(45) Date of Patent: Jun. 1, 2021

(54) ORAL CARE DEVICE

(71) Applicant: Colgate-Palmolive Company, New York, NY (US)

(72) Inventors: Patrik Johansson, Hoboken, NJ (US); Leighton Davies-Smith, Lebanon, NJ (US)

(73) Assignee: Colgate-Palmolive Company, New York, NY (US)

( * ) Notice: Subject to any disclaimer, the term of this patent is extended or adjusted under 35 U.S.C. 154(b) by 27 days.

(21) Appl. No.: 16/436,295

(22) Filed: Jun. 10, 2019

(65) Prior Publication Data

US 2019/0374018 A1  Dec. 12, 2019

Related U.S. Application Data

(60) Provisional application No. 62/683,167, filed on Jun. 11, 2018.

(51) Int. Cl.
*A46B 15/00* (2006.01)
*A46B 11/00* (2006.01)
(Continued)

(52) U.S. Cl.
CPC ...... *A46B 15/0022* (2013.01); *A46B 15/0024* (2013.01); *A46B 11/002* (2013.01);
(Continued)

(58) Field of Classification Search
CPC .............. A46B 11/002; A46B 15/0022; A46B 15/0024; A46B 2200/1066; A61C 17/221;
(Continued)

(56) References Cited

U.S. PATENT DOCUMENTS

| 3,520,297 A | 7/1970 | Bechtold |
| 4,969,868 A | 11/1990 | Wang |

(Continued)

FOREIGN PATENT DOCUMENTS

| CA | 2154860 | 1/1996 |
| CN | 200953928 | 10/2007 |

(Continued)

OTHER PUBLICATIONS

International Search Report and Written Opinion mailed in International Application No. PCT/US2015/067121 dated Jun. 24, 2016.

(Continued)

*Primary Examiner* — Marc Carlson

(57) ABSTRACT

An oral care device may include: a body including a head; a plurality of teeth cleaning elements extending from the head; a first electrode on the head; a second electrode on the head and spaced apart from the first electrode, wherein at least one of the first and second electrodes is a sacrificial electrode; a power source; and a controller configured to operably couple the power source to the first and second electrodes to create an electric potential between the first and second electrodes so that ions are released from the sacrificial electrode during a brushing session; wherein the controller is configured to change a magnitude of the electric potential the brushing session ends.

18 Claims, 6 Drawing Sheets

(51) Int. Cl.
*A61C 17/22* (2006.01)
*A61C 17/32* (2006.01)

(52) U.S. Cl.
CPC ..... *A46B 2200/1066* (2013.01); *A61C 17/221* (2013.01); *A61C 17/222* (2013.01); *A61C 17/32* (2013.01)

(58) Field of Classification Search
CPC ..... A61C 17/222; A61C 17/32; A61C 19/063; A61N 1/0436; A61N 1/0548; A61N 1/325
See application file for complete search history.

(56) References Cited

U.S. PATENT DOCUMENTS

| | | |
|---|---|---|
| 5,372,501 A | 12/1994 | Shalvi |
| 5,824,292 A | 10/1998 | Carr et al. |
| 5,921,251 A | 7/1999 | Joshi |
| 6,135,126 A | 10/2000 | Joshi |
| 6,341,400 B1 | 1/2002 | Kobayashi et al. |
| 6,955,538 B1 | 10/2005 | Borch et al. |
| 7,479,133 B2 | 1/2009 | Sun et al. |
| 7,775,795 B2 | 8/2010 | Khawaled et al. |
| 7,857,620 B2 | 12/2010 | Shih |
| 7,886,398 B2 | 2/2011 | Morita et al. |
| 7,975,341 B2 | 7/2011 | Cai et al. |
| 8,156,602 B2 | 4/2012 | Jimenez et al. |
| 8,295,923 B2 | 10/2012 | Eischen et al. |
| 8,595,882 B2 | 12/2013 | Bax et al. |
| 8,668,397 B2 | 3/2014 | Barkhordar |
| 8,708,700 B2 | 4/2014 | Jimenez et al. |
| 8,734,421 B2 | 5/2014 | Sun et al. |
| 9,009,901 B2 | 4/2015 | Doll et al. |
| 9,125,484 B2 | 9/2015 | Gatzemeyer |
| 9,192,762 B2 | 11/2015 | Doll et al. |
| 9,445,878 B2 | 9/2016 | Jimenez et al. |
| 9,497,025 B2 | 11/2016 | Alsup |
| 9,597,496 B1 | 3/2017 | Johansson et al. |
| 10,179,038 B2 * | 1/2019 | Johansson ............ A61C 17/005 |
| 2007/0071541 A1 | 3/2007 | Vila |
| 2009/0070949 A1 | 3/2009 | Sagel et al. |
| 2012/0096657 A1 | 4/2012 | So et al. |
| 2013/0224679 A1 | 8/2013 | Teggatz et al. |
| 2014/0245553 A1 | 9/2014 | Gravina |
| 2015/0105712 A1 | 4/2015 | Pongpeerapat |
| 2016/0184065 A1 * | 6/2016 | Johansson .......... A46B 15/0002 433/216 |
| 2016/0354188 A1 | 12/2016 | Jimenez et al. |
| 2017/0189152 A1 * | 7/2017 | Johansson ............... C25B 11/02 |
| 2019/0008271 A1 * | 1/2019 | Gontarz .................... C25B 9/06 |

FOREIGN PATENT DOCUMENTS

| | | |
|---|---|---|
| DE | 102005009958 | 1/2007 |
| EP | 1508323 | 2/2005 |
| JP | 2009-045202 A | 3/2009 |
| WO | 2001/030198 | 5/2001 |
| WO | 2007/047568 | 4/2007 |
| WO | 2009/066647 | 5/2009 |
| WO | 2009/148442 | 12/2009 |
| WO | 2013/141359 | 9/2013 |
| WO | 2016/087675 | 6/2016 |
| WO | 2016/106223 | 6/2016 |
| WO | 2017/116400 | 7/2017 |

OTHER PUBLICATIONS

International Search Report and Written Opinion of the International Searching Authority in International Application No. PCT/US2018/038944, dated Nov. 14, 2018.

International Search Report of the International Searching Authority issued in International Application PCT/US2016/068691 dated Mar. 13, 2017.

International Search Report and Written Opinion of the International Searching Authority in International Application PCT/US2019/036320, dated Aug. 21, 2019.

* cited by examiner

ORAL CARE DEVICE

CROSS-REFERENCE TO RELATED APPLICATIONS

The present application claims priority to U.S. Provisional Patent Application Ser. No. 62/683,167, filed on Jun. 11, 2019, the entirety of which is incorporated herein by reference.

BACKGROUND

Oral care devices are known which provide oral health benefits through the release of ions from sacrificial electrodes. Some types of beneficial ions, however, may be poor tasting to users during oral care sessions. There is therefore a need for improvements to such oral care devices, and the processes by which they operate, in order to help reduce negative taste sensations a user might experience when the beneficial ions are introduced into their oral care routine.

BRIEF SUMMARY

Exemplary embodiments according to the present disclosure are directed to an oral care device that includes one or more sacrificial electrodes for purposes of introducing beneficial ions into the oral cavity when the oral care device is used. Particularly, the oral care device includes a controller which controls an electric potential between two electrodes, at least one of which is a sacrificial electrode, in order to control the release rate of ions during the brushing session and reduce negative tastes sensations that may be experienced by the user. The release rate of the ions may be highest early in the brushing session, when the user has the most fluid and toothpaste in their mouth to mask the taste of the ions and decreasing thereafter. The release rate of the ions may be controlled by decreasing the electric potential between the electrodes during the brushing session. Alternatively, the release rate may be highest at the end of the brushing session to leave residual ions in the mouth to help improve oral health. In still other alternatives, the release rate may be changed in any manner during the brushing session. The method of control advantageously leads to controlling the release rate of the ions during the brushing session so that the release rate changes during the brushing session.

In one aspect, the invention can be an oral care device which includes: a body including a head; a plurality of teeth cleaning elements extending from the head; a first electrode on the head; a second electrode on the head and spaced apart from the first electrode, wherein at least one of the first and second electrodes is a sacrificial electrode; a power source; and a controller configured to operably couple the power source to the first and second electrodes to create an electric potential between the first and second electrodes so that ions are released from the sacrificial electrode during a brushing session; wherein the controller is configured to change a magnitude of the electric potential before the brushing session ends.

In another aspect, the invention can be an oral care method which includes: generating an electric potential between a first electrode and a second electrode on a head of an oral care device and positioned spaced apart from each other, wherein at least one of the first and second electrodes is a sacrificial electrode, the electric potential resulting in ions being released from the sacrificial electrode during a brushing session; and changing a magnitude of the electric potential before the brushing session ends.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The foregoing summary, as well as the following detailed description of the exemplary embodiments, will be better understood when read in conjunction with the appended drawings. It should be understood, however, that the invention is not limited to the precise arrangements and instrumentalities shown in the following figures.

DETAILED DESCRIPTION

Figure 1:
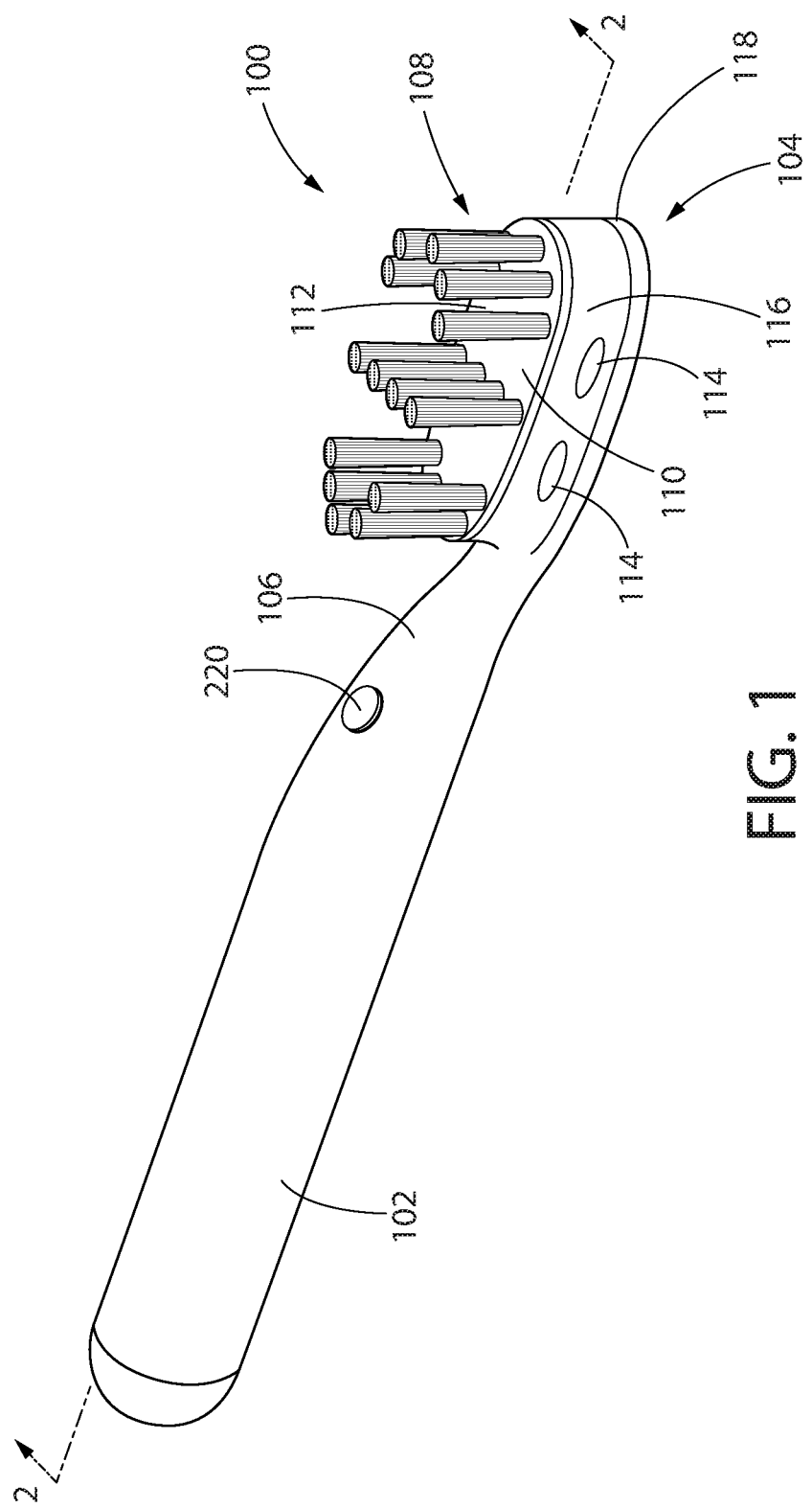
FIG. 1 is a perspective view of an oral care device including at least one sacrificial electrode in accordance with the present invention.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top" and "bottom" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," and similar refer to a relationship wherein structures are secured or attached to one another either directly or indirectly through intervening structures, as well as both movable or rigid attachments or relationships, unless expressly described otherwise. Moreover, the features and benefits of the invention are illustrated by reference to the preferred embodiments. Accordingly, the invention expressly should not be limited to such preferred embodiments illustrating some possible non-limiting combinations of features that may exist alone or in other combinations of features; the scope of the invention being defined by the claims appended hereto.

Features of the present invention may be implemented in software, hardware, firmware, or combinations thereof. The programmable processes described herein are not limited to any particular embodiment, and may be implemented in an operating system, application program, foreground or background processes, driver, or any combination thereof.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Turning in detail to the drawings, FIG. 1 illustrates an oral care device as a toothbrush 100 in accordance with an exemplary embodiment. The toothbrush 100 includes a handle 102, a head 104 disposed at the distal end of the handle 102, and a neck portion 106 disposed between the handle 102 and the head 104. The handle 102 has a generally elongate shape, along a longitudinal axis. In alternative embodiments, one or more of the handle 102, the head 104, and/or the neck 106 may have different shapes, sizes, orientations, and/or the like. The invention is not to be limited by the size and/or shape of any portion of the toothbrush 100 unless otherwise indicated in the claims. Additional features may also be incorporated into the toothbrush or disposed on the toothbrush. In other embodiments, the oral care device may be a toothbrush which includes a head that detaches from the handle, such that the head is replaceable with another head. In still other embodiments, the oral care device may be any other type of oral care implement.

In the embodiment illustrated in FIG. 1, the head 106 of the toothbrush 100 also includes a plurality of teeth cleaning elements 108 extend from a support plate 110. As used herein, the term "teeth cleaning elements" includes any type of structure that is commonly used for or is suitable for use in providing oral health benefits (e.g., tooth cleaning, tooth polishing, tooth whitening, massaging, stimulating, etc.) by making intimate contact with portions of the teeth and/or gums. Such teeth cleaning elements include but are not limited to tufts of bristles that can be formed to have a number of different shapes, sizes, and relative configurations, massage elements, and elastomeric cleaning members that can be formed to have a number of different shapes and sizes, or a combination of both tufts of bristles and elastomeric cleaning members. The teeth cleaning elements 108 may be arranged on the support plate 110 in many configurations.

In FIG. 1, the teeth cleaning elements 108 include bristles, which may be formed as bristle tufts. The tufts may be formed with bristles of the same or different bristle materials (such as nylon bristles, spiral bristles, rubber bristles, etc.). Moreover, while the teeth cleaning elements 108 may be arranged so that they are generally perpendicular to the top surface 112 of the support plate 110, some or all of the tooth cleaning elements may be angled with respect to the top surface 112 and/or with respect to each other. When the teeth cleaning elements 108 includes bristle tufts, it is thereby possible to select the combination of bristle configurations, bristle materials, and/or bristle orientations to achieve specific intended results and operational characteristics, thus maximizing and enhancing cleaning, tooth polishing, tooth whitening, massaging, stimulation, and the like.

The teeth cleaning elements 108 may be attached to the support plate 110 by any method, conventional or otherwise. In certain embodiments, the support plate 110 may include a plurality of holes formed there through, and the teeth cleaning elements 108 may be mounted to the support plate 110 within the holes. This type of technique for mounting the teeth cleaning elements 108 to the support plate 110 is generally known as anchor free tufting (AFT). In AFT a plate (often referred to as a head plate) or membrane is created and the teeth cleaning elements (such as bristles, elastomeric elements, and combinations thereof) are positioned into the head plate so as to extend through the holes of the head plate. The free ends of the teeth cleaning elements on one side of the head plate perform the cleaning function. The ends of the teeth cleaning elements on the other side of the head plate are melted together by heat to be anchored in place. As the teeth cleaning elements are melted together, a melt matte is formed, which is a layer of plastic formed from the collective ends of the teeth cleaning elements that connects the teeth cleaning elements to one another on one side of the head plate and prevents the teeth cleaning elements from being pulled through the tuft holes.

In example shown, after the teeth cleaning elements 108 are secured to the support plate 110, the support plate 110 is secured to the head 104. Ultrasonic welding is one technique that may be used to secure the support plate 110 to the head 104, although other techniques may also be used. When the support plate 110 is coupled to the head 104, the melt matte is located between a lower surface of the support plate 110 and a floor of a basin or cavity of the head 104 in which the support plate 110 is disposed. The melt matte, which is coupled directly to and in fact forms a part of the teeth cleaning elements 108, prevents the teeth cleaning elements 108 from being pulled through the holes in the support plate 110, thus ensuring that the teeth cleaning elements 108 remain attached to the support plate 110 during use of the oral care device 100.

In other embodiments, the teeth cleaning elements 108 may be connected to the support plate 110 or a membrane later incorporated using a technique known in the art as AMR. Generally speaking, in this technique, a head plate is provided and the bristles are inserted into holes in the head plate so that free/cleaning ends of the bristles extend from the front surface of the head plate and bottom ends of the bristles are adjacent to the rear surface of the head plate. After the bristles are inserted into the holes in the head plate, the bottom ends of the bristles are melted together by applying heat thereto, thereby forming a melt matte at the rear surface of the head plate. The melt matte is a thin layer of plastic that is formed by melting the bottom ends of the bristles so that the bottom ends of the bristles transition into a liquid, at which point the liquid of the bottom ends of the bristles combine together into a single layer of liquid plastic that at least partially covers the rear surface of the head plate. After the heat is no longer applied, the melted bottom ends of the bristles solidify/harden to form the melt matte/thin layer of plastic. In some conventional applications, after formation of the melt matte, a tissue cleaner is injection molded onto the rear surface of the head plate, thereby trapping the melt matte between the tissue cleaner and the rear surface of the head plate. Other structures may be coupled to the rear surface of the head plate to trap the melt matte between the rear surface of the head plate and such structure without the structure necessarily being a tissue cleaner. For example, a structure covering the melt matte may be a plastic material that is used to form a smooth rear surface of the head, or the like. Alternatively, the structure can be molded onto the rear surface of the head plate or snap-fit (or other mechanical coupling) to the rear surface of the head plate as desired.

Of course, techniques other than AFT and AMR can be used for mounting teeth cleaning elements 108 to the support plate 110, such as widely known and used stapling/anchoring techniques or the like. In such embodiments the teeth cleaning elements 108 may be coupled directly to the support plate 110. Furthermore, in a modified version of the AFT process discussed above, the support plate 110 may be formed by positioning the teeth cleaning elements 108 within a mold, and then molding the support plate 110 around the teeth cleaning elements 108 via an injection molding process.

Moreover, in certain embodiments, various combinations of stapled, IMT, AMR, or AFT cleaning elements may be used. Alternatively, the teeth cleaning elements 108 could be mounted to tuft blocks or sections by extending through suitable openings in the tuft blocks so that the base of the teeth cleaning elements 108 is mounted within or below the tuft block. In still other embodiments, likely in which the tooth cleaning elements are not bristles, the teeth cleaning elements 108 may be molded integrally with the support plate 110.

The head 104 also includes a plurality of apertures 114 which are disposed through a sidewall 116 of the head 104 and provide a channel or passageway through the sidewall 116. Such a channel may allow for fluid communication between the inner cavity of the head 104 of the toothbrush 100 and the environment external to the head 104. The cavity, which may be bounded by the support plate 110, the sidewall 104 and a base 118, is discussed in more detail below. In certain embodiments, the head 104 may be constructed without the cavity.

Figure 2:
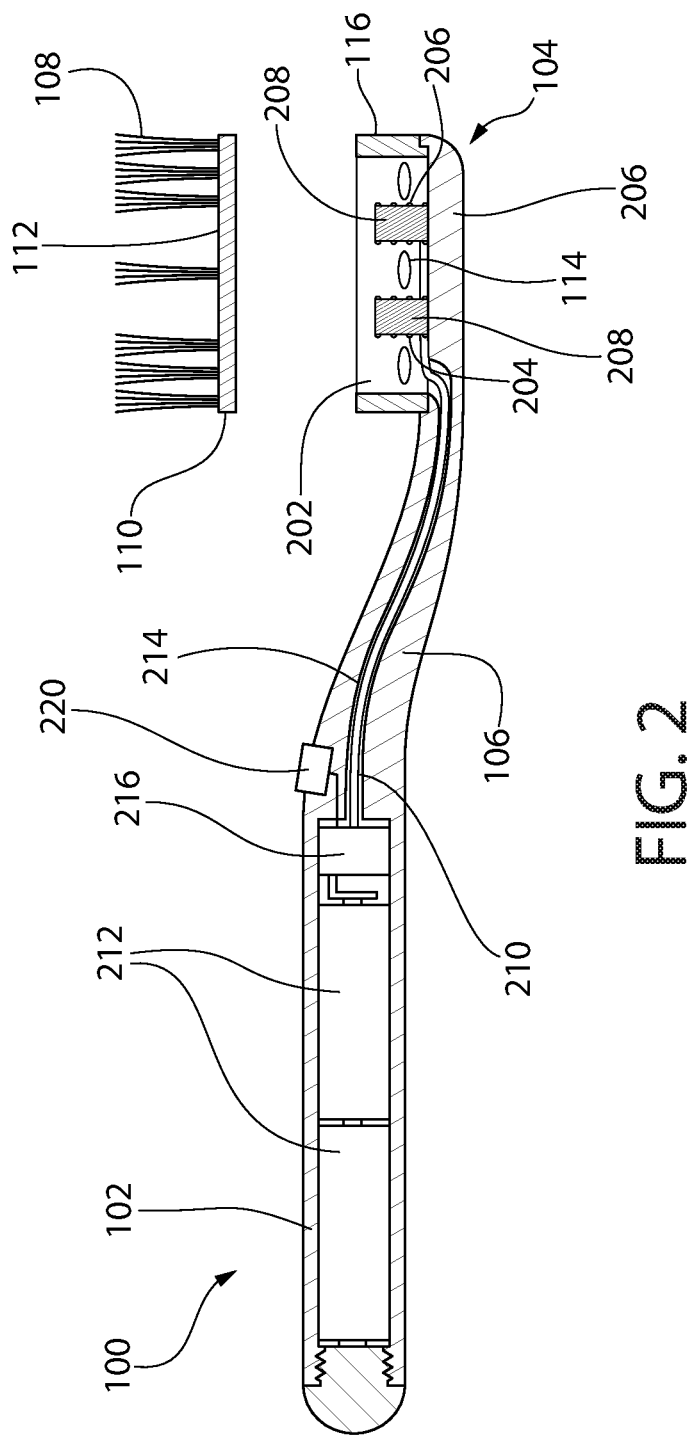
FIG. 2 is an exploded cross-sectional view of the oral care device taken along the section line 2-2 in FIG. 1.

FIG. 2 shows an exploded, cross-section of the toothbrush 100. In this view, the cavity 202 formed by the head 104 is shown. The cavity 202 is a basin or void defined by the sidewall 116 that extends upwardly from the base 118 of the head 104. A first electrode 204 and a second electrode 206 are placed on the head 104 within the cavity 202 and spaced apart from each other. At least one of the first electrode 204 and the second electrode 206 is a sacrificial electrode. As is detailed further below, when only one of the first electrode 204 or the second electrode 206 is a sacrificial electrode, the sacrificial electrode is operated as an anode and the non-sacrificial electrode is operated as a cathode; when both of the first electrode 204 and the second electrode 206 are sacrificial electrodes, one is operated as an anode while the other is operates as a cathode, with the polarity of the electric potential between the first and second electrodes 204, 206 determining the operational state of each.

The support plate 110 is positioned relative to the head 104 to cover the cavity 202, thereby enclosing the electrodes 204, 206 in the cavity 202. In certain embodiments, the support plate 110 may be fixed at a distal end of the sidewall 116, e.g., by an adhesive, welding, or other mechanical means. In embodiments in which the head 104 does not include the cavity 202, the first and second electrodes 204, 206 may be placed on any surface of the head 104, with the first and second electrodes 204, 206 still positioned spaced apart from each other. In certain other embodiments, one or both of the first and second sacrificial electrodes 204, 206 may be placed on the neck portion 106 of the toothbrush 100. The invention is not to be limited by the placement of either of the first and second sacrificial electrodes 204, 206, whether on the head 104 or on the neck portion 106 of the toothbrush 100, unless otherwise expressly stated in the claims.

The electrodes 204, 206 may be any known shape or configuration. As shown, the electrodes 204, 206 are formed as electrical coils, and include a number of turns of a metallic wire wound about separate cores 208. The cores 208 may be formed integrally with the base or may be formed separately and subsequently fixed to the base. In other embodiments, the cores 208 may not be present at all. In other embodiments, the electrodes 204, 206 may be formed as metal plates or other spaced-apart metal fixtures. Regardless of their shape or configuration, in certain embodiments the electrodes 204, 206 may be formed of 90% or more of the metal making up the electrode.

As indicated, at least one of the electrodes 204, 206 is a sacrificial electrode, in that at least one of the electrodes 204, 206 includes a sacrificial metal. When an electric potential (i.e., a voltage difference) of appropriate polarity is generated between the first and second electrodes 204, 206, the sacrificial electrode will give up ions, e.g., by oxidizing. In certain embodiments, at least one of the electrodes 204, 206 includes zinc or a zinc alloy, and the presence of an electric potential oxidizes the zinc to release $Zn^{2+}$. Zinc ions are conventionally known to provide oral health benefits including, e.g., anti-bacterial benefits. In the embodiment of FIG. 1, zinc ions are given off in the cavity 202 of the head 104 of the toothbrush 100, and once released from one or both of the electrodes 204, 206 to the cavity 202, the beneficial zinc ions enter the oral cavity via the apertures 114. In certain embodiments, one or both of the electrodes 204, 206 may be formed of materials other than zinc and zinc alloys.

In certain embodiments in which both the first and second electrodes 204, 206 are a sacrificial electrode, each electrode 204, 206 may include a different sacrificial metal. In certain embodiments, one or both of the electrodes 204, 206 may be formed of different metals that can be oxidized to provide ions that give alternative oral benefits. For example, Tin ions, i.e., $Sn^{2+}$ and $Sn^{4+}$, have known oral health benefits, such that one or both of the electrodes 204, 206 could include Tin. In certain other embodiments, the oxidation of iron and/or manganese can drive the formation of hydroxide radicals from hydrogen peroxide, e.g., via the fenton reaction, which may provide other benefits in the oral cavity, such that one or both of the electrodes 204, 206 could include iron or manganese.

In the embodiment shown, the apertures 114 also allow fluids, e.g., saliva and water, in the external environment to enter the cavity 202. Once in the cavity 202, the fluids may act as an electrolyte to promote the release of the ions from at least one of the electrodes 204, 206 upon generation of an electric potential therebetween.

Conductive leads 210 connect each of the electrodes 204, 206 to the control circuit 216, which is in turn operably coupled to a power source 212, shown as a pair of batteries disposed in the handle 102. A switch 220 controls providing power from the power source 212 to the control circuit 216. The conductive leads 210 extend from the electrodes 204, 206 through the neck 106 and into the handle 102 via a passageway or channel 214 connected to the cavity 202 of the head 104. The conductive leads 210 electrically couple to the control circuit 216, which controls the voltage applied from the power source 212 to the electrodes 204, 206.

In certain embodiments, the power source 212 may be external to the toothbrush 100. In still other embodiments, the power source 212 be rechargeable batteries. In still other embodiments, the power source 212 may be any other type of power storage or power-providing electricity source which also provides a ground or negative terminal.

The control circuit 216 generates an electric potential between the two electrodes 204, 206 by maintaining each electrode 204, 206 at a different voltage. By doing so, one of the two electrodes 204, 206 serves as an effective anode, and the other serves as an effective cathode. In embodiments in which only one of the electrodes 204, 206 is a sacrificial electrode, the electric potential will always have the same polarity. In embodiments in which both the electrodes 204, 206 are a sacrificial electrode, then the electric potential may be switched between a positive polarity and a negative polarity to control which one of the two electrodes 204, 206 is operated as the anode. Although both electrodes 204, 206 are formed as sacrificial electrodes, such that both are capable of releasing ions under certain conditions, only the one of the electrodes 204, 206 operating as the anode releases ions—the other of the electrodes 204, 206 operating as the cathode does not release ions. In the toothbrush 100 shown, the electric potential is created between the electrodes 204, 206 by the control circuit 216 electrically coupling one of the electrodes 204, 206 to the positive terminal of the power source 212 and electrically coupling the other of the electrodes 204, 206 to the negative terminal of the power source 212.

Although one pair of electrodes is illustrated in FIG. 2, additional pairs of electrodes may also be present. For example, a first pair of sacrificial electrodes may be formed using zinc as the sacrificial metal, and a second pair of sacrificial electrodes may be formed using iron as the sacrificial metal. In such embodiments, the control circuit 216 may be used to create an electric potential between both pairs of electrodes, either simultaneously for both pair of sacrificial electrodes, or alternatively, which each pair having an electric potential between them while the other pair is decoupled from the power source 212. In other embodiments, multiple pairs of sacrificial electrodes may be included, with all the sacrificial electrodes being formed of the same sacrificial metal, such that the increased number enables an increased release rate of ions.

Figure 3:
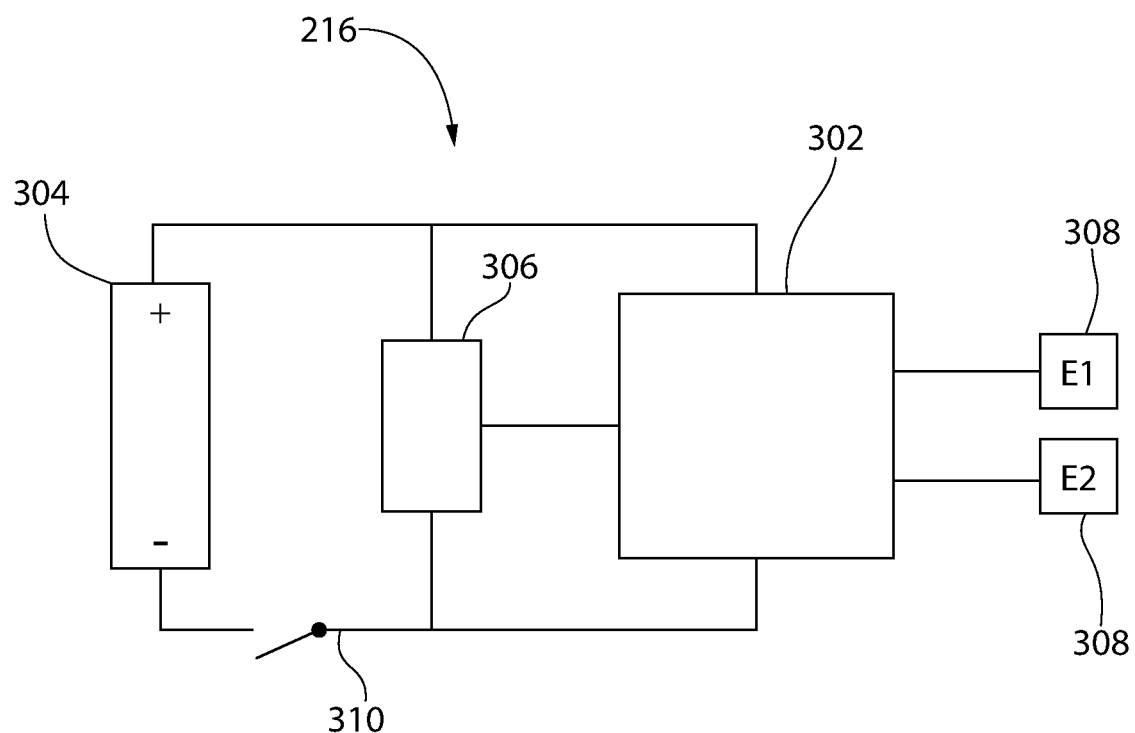
FIG. 3 is a schematic view of a control circuit for at least one sacrificial electrode in an oral care device.

FIG. 3 illustrates the control circuit 216 of the toothbrush 100. The control circuit 216 includes a controller 302, an oscillator 306, and a switch 310. The control circuit 216 is operably coupled to the power source 304 and to the two electrodes 308, identified as E1 and E2, at least one of which is a sacrificial electrode. The controller 302 may be a programmable device which implements the operational features of the oral care device, as described herein, in software, hardware, firmware, or combinations thereof. In certain embodiments, the controller 302 may be implemented as an electronic sub-circuit which is assembled to perform the operational features of the oral care device as described herein.

The switch 310 operably couples the controller 302 and the oscillator 306 the power source 304. When the switch 310 is in the open position, power is not provided to the controller 302 or the oscillator 306, and the controller 302 is in the OFF state. When the switch is in the closed position, power is provided to both the controller 302 and the oscillator 306, and the controller 302 is in the ON state. When the oscillator 306 is powered, the oscillator 306 provides a clock signal to the controller 302. In certain embodiments, the oscillator 306 is a linear oscillator that produces a sinusoidal output. The output of the oscillator 306 may take any periodic waveform having a constant period, such that the constant period may be used by the controller 302 to measure time. As described below, the controller 302 may use the clock signal as a timer to determine when to change the magnitude of the electric potential. In embodiments with two sacrificial electrodes, the controller 302 may use the clock signal as a timer to determine when to perform polarity switching for the electric potential between the electrodes 308. In certain embodiments, the oscillator 306 may be omitted from the control circuit 216. In certain other embodiments, the oscillator 306 may be integrated as part of the controller 302.

When the controller 302 is in the ON state, the controller 302 electrically couples one of the electrodes 308 to the positive terminal of the power source 304 and the other of the electrodes 308 to the negative terminal of the power source 304. In embodiments in which only one of the electrodes 308 is a sacrificial electrode, the sacrificial electrode is electrically coupled to the negative terminal of the power source 304. In embodiments in which both of the electrodes 308 are sacrificial electrodes, either one is initially electrically coupled to the negative terminal of the power source 304. By coupling the electrodes 308 to the power source 304 in this manner, an electric potential is generated between the electrodes 308. The electric potential generated between the electrodes 308 may be characterized as the combination of a magnitude, which is representative of the absolute value of the voltage potential between the electrodes 308, and positive polarity or negative polarity, which is representative of the direction of current flow between the electrodes 308. When the electric potential between the electrodes 308 has a positive polarity, one of the electrodes 308 serves as the anode and the other serves as the cathode, and when the electric potential has a negative polarity, the electrodes 308 reverse their functions as cathode and anode. Only the electrode 308 that is a sacrificial electrode and operating as the anode releases ions. For purposes of convenience for this description, an electric potential with a positive polarity is generated by the control circuit 216 of FIG. 3 when the electrode E1 is electrically coupled to the positive terminal of the power source 304 and the electrode E2 is electrically coupled to the negative terminal of the power source 304. Likewise, an electric potential with a negative polarity is generated by the control circuit of FIG. 3 when the electrode E1 is electrically coupled to the negative terminal of the power source 304 and the electrode E2 is electrically coupled to the positive terminal of the power source 304.

When the controller 302 transitions from the OFF state to the ON state, the controller 302 is configured to control the electric potential between the electrodes in accordance with a control function which causes the magnitude of the electric potential to change during the brushing session. The change may occur at any time before the brushing session ends, and the change is such that the magnitude of the electric potential increases, decreases, or increases and decreases (in any combination and number) before the brushing session ends. At the end of the brushing session, the magnitude of the electric potential changes one final time when the electrodes 308 are electrically decoupled from the power source 304 (i.e., the OFF state of the controller 302). In certain embodiments, the change in the magnitude of the electric potential may include a linear change. In certain other embodiments, the change in the magnitude of the electric potential may include a change in accordance with a polynomial function. In still other embodiments, the change in the magnitude of the electric potential may include a change in a plurality of discrete steps. In yet other embodiments, the change in the magnitude of the electric potential may include a combination of any two or more of the aforementioned methods of changing the magnitude of the electric potential. In certain embodiments, the time period that the controller is in the ON state is no greater than the time period of the brushing session, such that the controller 302 transitions to the OFF state when the user is done brushing. In certain other embodiments, the time period that the controller is in the ON state is no greater than the user brushing period. In certain embodiments, the time period that the controller is in the ON state is less than half of the user brushing period.

In certain embodiments, the brushing session may be a predetermined time period that is set before the toothbrush is used by the user. For example, in certain embodiments, the brushing session may be set to a time period of two minutes, which is the brushing session time that is generally recommended by oral health care professionals when practicing good oral hygiene. In certain other embodiments, the brushing session may be set to a time period of less than the generally recommended bushing session time of two minutes. In such embodiments, the brushing session may be set to any time period in the range of 1 second to two minutes, as predetermined before the toothbrush is used by the user. By way of example, the brushing session may be set to a time period in the range of 1 second to two minutes based on the experience and knowledge of a designer, engineer, or the like at the time of manufacture.

The user brushing period, as used herein, is any time period up to and including the time period of the brushing session. In certain embodiments, the user brushing period may be a predetermined time period that is set before the toothbrush is used by the user. For example, where the brushing session is set to a time period of two minutes, the user brushing period may likewise be set to a time period of two minutes. By way of another example, where the brushing session is set to a time period of less than two minutes, the user brushing period may be set to the same time period or a time period that is less than the brushing session. In certain embodiments, the user brushing period may be set to a time period based on the experience and knowledge of a designer, engineer, or the like at the time of manufacture. In certain other embodiments, the user brushing period may be set to a time period based on a collection of sample data. In such embodiments, the user brushing period may be set to the average brushing period as determined by the collected sample data.

FIGS. 4A-4D illustrate non-limiting examples of control functions in which the magnitude of the electric potential between the electrodes 308 is changed as a function of time when one of the electrodes 308 is a sacrificial electrode. FIGS. 5A-5D illustrate non-limiting examples of control functions in which the magnitude of the electric potential between the electrodes 308 is changed as a function of time when both of the electrodes 308 formed as sacrificial electrodes and may be alternately operated as the anode. In each of these figures, the magnitude is shown on the vertical axis and time is shown on the horizontal axis. In FIGS. 4A-4D, the electric potential always has the same polarity, so only a single polarity of the magnitude is shown. In FIGS. 5A-5D, the electric potential may have a positive polarity, which is represented by magnitudes above the horizontal axis, or a negative polarity, which is represented by magnitudes below the horizontal axis. And, although the control functions in FIGS. 5A-5D all begin with a positive polarity, in certain embodiments the control functions in embodiments with more than one sacrificial electrode may begin with a negative polarity. These control function examples are intended as examples only and are not intended to be limiting of the invention unless otherwise expressly stated in the claims.

Figure 4A:
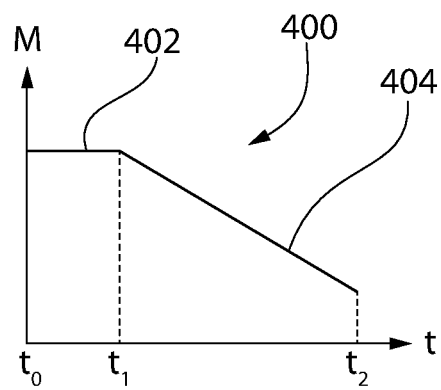
FIG. 4A is a graphical representation of a first control function for controlling the electric potential between two electrodes, with one of the electrodes operating as a sacrificial electrode.

FIG. 4A illustrates a non-limiting example of a control function 400 in which the magnitude of the electric potential between the electrodes 308 is changed linearly over time. The control function 400 begins at time $t_0$, when the controller 302 transitions to the ON state, and includes a constant magnitude section 402. During the period between $t_1$ and $t_2$, the control function 400 includes a linearly changing section 404. In certain embodiments, this linearly changing section 404 may change the magnitude by increasing the magnitude or by any combination of increasing and decreasing the magnitude. At time $t_2$, the controller 302 transitions to the OFF state, after which the magnitude of the electric potential goes to zero. The time period between $t_0$ and $t_2$ is no greater than the brushing session. In certain embodiments, the time period between $t_0$ and $t_2$ is no greater than the user brushing period, and it may be less than half of the user brushing period. Optionally for this control function 400, the constant magnitude section 402 may be omitted or moved to a different time within the control function 400, or additional constant magnitude sections and/or magnitude changing sections may be included.

Figure 4B:
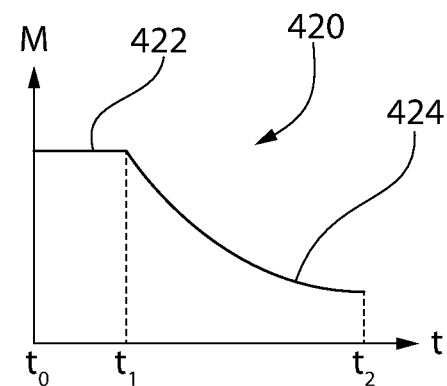
FIG. 4B is a graphical representation of a second control function for controlling the electric potential between two electrodes, with one of the electrodes operating as a sacrificial electrode.

FIG. 4B illustrates a non-limiting example of a control function 420 in which the magnitude of the electric potential between the electrodes 308 is changed in accordance with a polynomial function. The control function 420 begins at time $t_0$, when the controller 302 transitions to the ON state, and includes a constant magnitude section 422. During the period between $t_1$ and $t_2$, the control function 420 includes a curved section 404 which curves according to a polynomial function and serves to decrease the magnitude in this example. The nature and curvature of the polynomial function, and whether the polynomial function increases, decreases, or any combination increases and decreases the magnitude, is not to be limiting of the invention unless otherwise expressly stated in the claims. At time $t_2$, the controller 302 transitions to the OFF state, after which the magnitude of the electric potential goes to zero. The time period between $t_0$ and $t_2$ is no greater than the brushing session. In certain embodiments, the time period between $t_0$ and $t_2$ is no greater than the user brushing period, and it may be less than half of the user brushing period. Optionally for this control function 420, the constant magnitude section 422 may be omitted or moved to a different time within the control function 420, or additional constant magnitude sections and/or magnitude changing sections may be included.

Figure 4C:
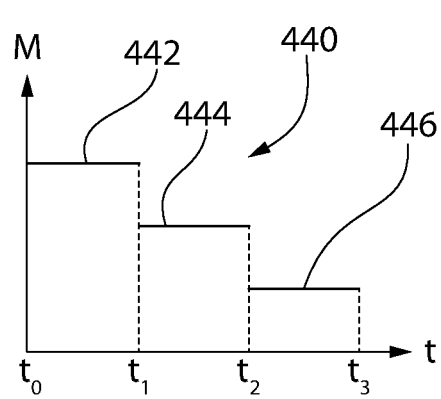
FIG. 4C is a graphical representation of a third control function for controlling the electric potential between two electrodes, with one of the electrodes operating as a sacrificial electrode.

FIG. 4C illustrates a non-limiting example of a control function 440 in which the magnitude of the electric potential between the electrodes 308 is changed in a plurality of discrete steps. The control function 440 begins at time $t_0$, when the controller 302 transitions to the ON state, and includes a first constant magnitude section 442. Between the time $t_1$ and $t_2$, the control function 440 includes a second constant magnitude section 444, and this second constant magnitude section 444 is at a magnitude that is less than the magnitude of the first constant magnitude section 442. Between the time $t_2$ and $t_3$, the control function 440 includes a third constant magnitude section 446, and this third constant magnitude section 446 is at a magnitude that is less than the magnitude of the second constant magnitude section 444. At time $t_3$, the controller 302 transitions to the OFF state, after which the magnitude of the electric potential goes to zero. Although the magnitude sections 442, 444, 446 are shown in a series of decreasing magnitude steps, in certain embodiments the step between any two or more of the magnitude sections may serve to increase the magnitude between the respective sections. The time period between $t_0$ and $t_3$ is no greater than the brushing session. In certain embodiments, the time period between $t_0$ and $t_3$ is no greater than the user brushing period, and it may be less than half of the user brushing period. Optionally for this control function 440, any of the constant magnitude sections may be omitted or moved to different times within the control function 440, or additional constant magnitude sections and/or magnitude changing sections may be included.

Figure 4D:
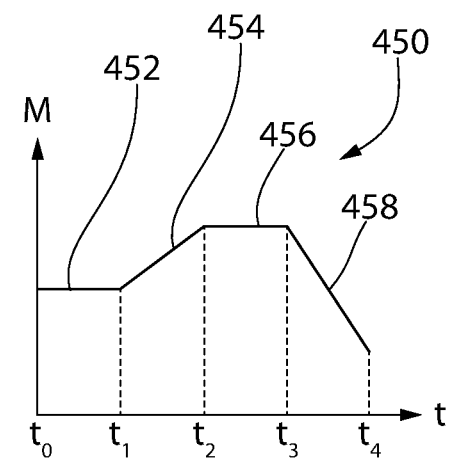
FIG. 4D is a graphical representation of a fourth control function for controlling the electric potential between two electrodes, with one of the electrodes operating as a sacrificial electrode.

FIG. 4D illustrates a non-limiting example of a control function 450 in which the magnitude of the electric potential between the electrodes 308 is changed by both increasing and decreasing during the brushing session. The control function 450 begins at time $t_0$, when the controller 302 transitions to the ON state, and includes a first constant magnitude section 452. Between the time $t_1$ and $t_2$, the control function 450 includes a first magnitude changing section 454, and this first magnitude changing section 454 linearly increases the magnitude. Between the time $t_2$ and $t_3$, the control function 450 includes a second constant magnitude section 456, and this second constant magnitude section 456 is at a magnitude that is greater than the magnitude of the first constant magnitude section 452. Between the time $t_3$ and $t_4$, the control function 450 includes a second magnitude changing section 458, and this second magnitude changing section 458 linearly decreases the magnitude in this example. At time $t_4$, the controller 302 transitions to the OFF state, after which the magnitude of the electric potential goes to zero. Although the magnitude increasing section 454 and the magnitude decreasing section 458 are shown as linearly increasing and decreasing the magnitude, respectively, in certain embodiments the increasing and decreasing may be achieved by application of a polynomial function. The time period between $t_0$ and $t_4$ is no greater than the brushing session. In certain embodiments, the time period between $t_0$ and $t_4$ is no greater than the user brushing period, and it may be less than half of the user brushing period. Optionally for this control function 450, any of the constant magnitude sections or the magnitude changing sections may be omitted or moved to different times within the control function 450, or additional constant magnitude sections and/or magnitude changing sections may be included.

Figure 5A:
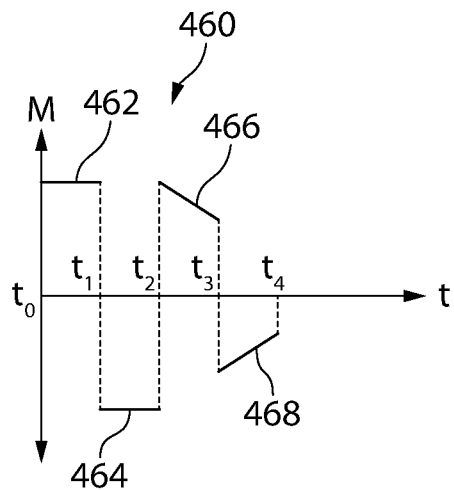
FIG. 5A is a graphical representation of a fifth control function for controlling the electric potential between two electrodes, the electrodes alternately operating as a sacrificial electrode.

FIG. 5A illustrates a non-limiting example of a control function 460 in which the magnitude of the electric potential between the electrodes 308 is changed linearly over time while the electric potential is switched between the positive polarity and the negative polarity. The control function 460 begins at time $t_0$, when the controller 302 transitions to the ON state, and includes a first constant magnitude section 462 having a positive polarity. During the period between $t_1$ and $t_2$, the control function 460 includes a second constant magnitude section 464 having a negative polarity, and this second constant magnitude section 464 is at a magnitude that is the same as the magnitude of the first constant magnitude section 462. During the period between $t_2$ and $t_3$, the control function 460 includes a first linearly changing section 466 having a positive polarity, and in this linearly changing section 466 the magnitude is decreasing. During the period between $t_3$ and $t_4$, the control function 460 includes a second linearly changing section 468 having a negative polarity, and in this linearly changing section 468 the magnitude is decreasing. In certain embodiments, these linearly changing sections 466, 468 may change the magnitude by increasing the magnitude or by any combination of increasing and decreasing the magnitude. At time $t_4$, the controller 302 transitions to the OFF state, after which the magnitude of the electric potential goes to zero. The time period between $t_0$ and $t_4$ is no greater than the brushing session. In certain embodiments, the time period between $t_0$ and $t_4$ is no greater than the user brushing period, and it may be less than half of the user brushing period. Optionally for this control function 460, the constant magnitude sections 462, 464 may be omitted or moved to different times within the control function 460, or additional constant magnitude sections and/or magnitude changing sections may be included.

Figure 5B:
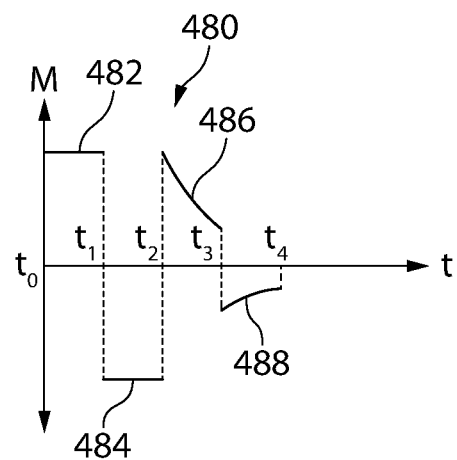
FIG. 5B is a graphical representation of a sixth control function for controlling the electric potential between two electrodes, the electrodes alternately operating as a sacrificial electrode.

FIG. 5B illustrates a non-limiting example of a control function 480 in which the magnitude of the electric potential between the electrodes 308 is changed according to a polynomial function over time while the electric potential is switched between the positive polarity and the negative polarity. The control function 480 begins at time $t_0$, when the controller 302 transitions to the ON state, and includes a first constant magnitude section 482 having a positive polarity. During the period between $t_1$ and $t_2$, the control function 480 includes a second constant magnitude section 484 having a negative polarity, and this second constant magnitude section 484 is at a magnitude that is the same as the magnitude of the first constant magnitude section 482. During the period between $t_2$ and $t_3$, the control function 480 includes a first curved section 486 which curves according to a polynomial function, has a positive polarity, and serves to decrease the magnitude in this example. During the period between $t_3$ and $t_4$, the control function 480 includes a second curved section 488 which curves according to a polynomial function, has a negative polarity, and serves to decrease the magnitude in this example. The nature and curvature of the polynomial functions 486, 488, and whether each polynomial function increases, decreases, or any combination increases and decreases the magnitude, is not to be limiting of the invention unless otherwise expressly stated in the claims. At time $t_4$, the controller 302 transitions to the OFF state, after which the magnitude of the electric potential goes to zero. The time period between $t_0$ and $t_4$ is no greater than the brushing session. In certain embodiments, the time period between $t_0$ and $t_4$ is no greater than the user brushing period, and it may be less than half of the user brushing period. Optionally for this control function 480, the constant magnitude sections 482, 484 may be omitted or moved to different times within the control function 480, or additional constant magnitude sections and/or magnitude changing sections may be included.

Figure 5C:
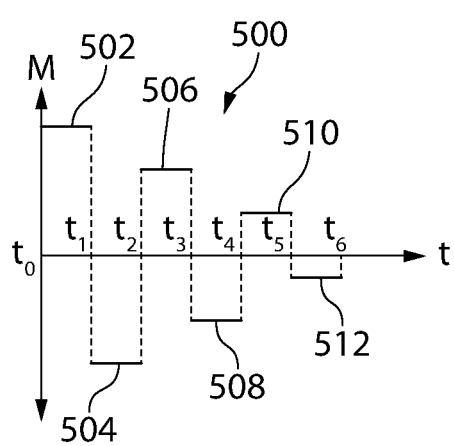
FIG. 5C is a graphical representation of a seventh control function for controlling the electric potential between two electrodes, the electrodes alternately operating as a sacrificial electrode.

FIG. 5C illustrates a non-limiting example of a control function 500 in which the magnitude of the electric potential between the electrodes 308 is changed in discrete steps over time while the electric potential is switched between the positive polarity and the negative polarity. The control function 500 begins at time $t_0$, when the controller 302 transitions to the ON state, and includes a first constant magnitude section 502 having a positive polarity. During the period between $t_1$ and $t_2$, the control function 500 includes a second constant magnitude section 504 having a negative polarity, and this second constant magnitude section 504 is at a magnitude that is less than the magnitude of the first constant magnitude section 502. During the period between $t_2$ and $t_3$, the control function 500 includes a third constant magnitude section 506 having a positive polarity, and this third constant magnitude section 506 is at a magnitude that is less than the magnitude of the second constant magnitude section 504. During the period between $t_3$ and $t_4$, the control function 500 includes a fourth constant magnitude section 508 having a negative polarity, and this fourth constant magnitude section 508 is at a magnitude that is less than the magnitude of the third constant magnitude section 506. During the period between $t_4$ and $t_5$, the control function 500 includes a fifth constant magnitude section 510 having a positive polarity, and this fifth constant magnitude section 510 is at a magnitude that is less than the magnitude of the fourth constant magnitude section 508. During the period between $t_5$ and $t_6$, the control function 500 includes a sixth constant magnitude section 512 having a negative polarity, and this sixth constant magnitude section 512 is at a magnitude that is less than the magnitude of the fifth constant magnitude section 510. At time $t_6$, the controller 302 transitions to the OFF state, after which the magnitude of the electric potential goes to zero. Although the magnitude is shown in this example in a series of decreasing magnitude steps, in certain embodiments the step between any two or more of the magnitude sections may serve to increase the magnitude between the respective sections. The time period between $t_0$ and $t_6$ is no greater than the brushing session. In certain embodiments, the time period between $t_0$ and $t_6$ is no greater than the user brushing period, and it may be less than half of the user brushing period. Optionally for this control function 500, any of the constant magnitude sections may be omitted or moved to different times within the control function 500, or additional constant magnitude sections and/or magnitude changing may be included.

Figure 5D:
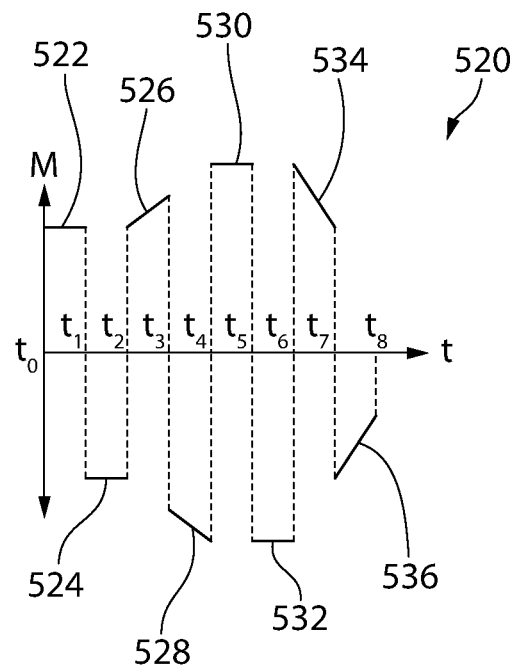
FIG. 5D is a graphical representation of an eighth control function for controlling the electric potential between two electrodes, the electrodes alternately operating as a sacrificial electrode.

FIG. 5D illustrates a non-limiting example of a control function 520 in which the magnitude of the electric potential between the electrodes 308 is changed by both increasing and decreasing during the brushing session. The control function 520 begins at time $t_0$, when the controller 302 transitions to the ON state, and includes a first constant magnitude section 522 having a positive polarity. During the period between $t_1$ and $t_2$, the control function 520 includes a second constant magnitude section 524 having a negative polarity. During the period between $t_2$ and $t_3$, the control function 520 includes a first magnitude changing section 526, and this first magnitude changing section 526 linearly increases the magnitude. During the period between $t_3$ and $t_4$, the control function 520 includes a second magnitude changing section 528 having a negative polarity, and this second magnitude changing section 528 linearly increases the magnitude. During the period between $t_4$ and $t_5$, the control function 520 includes a third constant magnitude section 530 having a positive polarity, and this third constant magnitude section 530 is at a magnitude that is greater than the magnitude of the first constant magnitude section 522. During the period between $t_5$ and $t_6$, the control function 520 includes a fourth constant magnitude section 532 having a negative polarity, and this fourth constant magnitude section 532 is at a magnitude that is greater than the magnitude of the second constant magnitude section 524. During the period between $t_6$ and $t_7$, the control function 520 includes a third magnitude changing section 534, and this third magnitude changing section 534 linearly decreases the magnitude in this example. During the period between $t_7$ and $t_8$, the control function 520 includes a fourth magnitude changing section 536 having a negative polarity, and this fourth magnitude changing section 536 linearly decreases the magnitude in this example. At time $t_8$, the controller 302 transitions to the OFF state, after which the magnitude of the electric potential goes to zero. Although the magnitude increasing sections 526, 528 and the magnitude decreasing sections 534, 536 are shown as linearly increasing and decreasing the magnitude, respectively, in certain embodiments the increasing and decreasing may be achieved by application of a polynomial function. The time period between $t_0$ and $t_8$ is no greater than the brushing session. In certain embodiments, the time period between $t_0$ and $t_8$ is no greater than the user brushing period, and it may be less than half of the user brushing period. Optionally for this control function 520, any of the constant magnitude sections or the magnitude changing sections may be omitted or moved to different times within the control function 520, or additional constant magnitude sections and/or magnitude changing may be included.

As indicated above, features of any two or more of the aforementioned examples may be combined to form a control function for controlling the electric potential between the electrodes.

As has been shown and described through the examples herein, the magnitude of the electric potential may be changed before the end of the brushing session. The change may be from a lower magnitude to a higher magnitude, from a higher magnitude to a lower magnitude, or any combination thereof. For example, it may be desirable for the magnitude of the electric potential to be reduced to zero in a time period that is less than half of the user brushing period so that the taste of the ion in the user's mouth is minimized following the brushing session. Alternatively, it may be desirable for the magnitude of the electric potential to be at a high point at the end of the brushing session so that there is a residual amount of the ion left in the user's mouth following the brushing session. In such applications, the ion may provide additional oral health benefits following brushing. As still another alternative, it may be desirable to have the time period of the greatest magnitude when there is the most toothpaste in the user's mouth, thereby masking the taste of the ion at its greatest concentration, and then reducing the magnitude at other time periods during the brushing session. The type of change in the magnitude of the electric potential and the manner in which the magnitude of the electric potential is changed is not to be limiting of the invention unless otherwise expressly stated in the claims.

Figure 6:
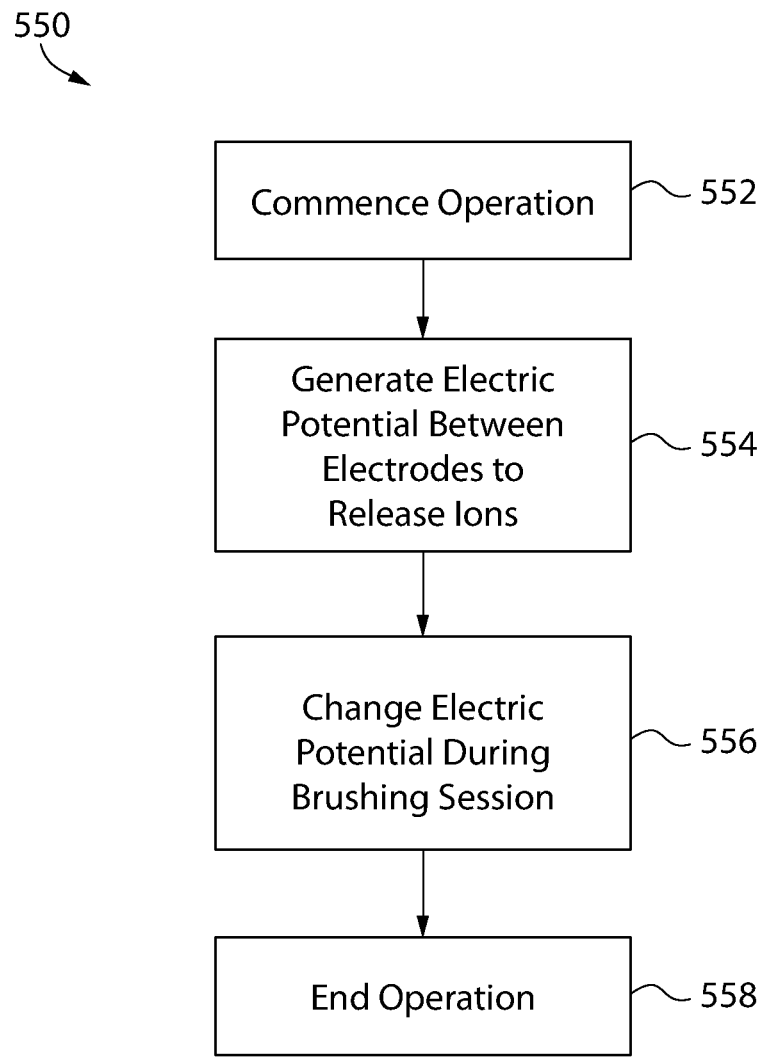
FIG. 6 is a flowchart showing an operating process for an oral care device including at least one sacrificial electrode.

FIG. 6 is a flowchart showing an operational process 550 that may be implemented with the control circuit 216. In the first step 552, the control circuit commences operation, and in the second step 554, the controller transitions from the OFF state to the ON state so that an electrical potential is generated between the electrodes, and the sacrificial electrode releases ions. In the third step 556, the magnitude of the electric potential is changed before the end of the brushing session. In certain embodiments, the magnitude of the electric potential is changed during a time period which is no greater than the user brushing period. In certain embodiments, the magnitude of the electric potential is changed during a time period which is less than half of the user brushing period. In this third step 556, the electric potential may be changed according to a control function, such as are described above. In the last step 558, the control circuit ends operation when the controller transitions from the ON state to the OFF state.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the invention has been described with respect to specific examples including presently preferred modes of carrying out the invention, those skilled in the art will appreciate that there are numerous variations and permutations of the above described systems and techniques. It is to be understood that other embodiments may be utilized and structural and functional modifications may be made without departing from the scope of the present invention. Thus, the spirit and scope of the invention should be construed broadly as set forth in the appended claims.

What is claimed is:

1. An oral care device comprising:
    a body comprising a head;
    a plurality of teeth cleaning elements extending from the head;
    a first electrode on the head;
    a second electrode on the head and spaced apart from the first electrode, wherein at least one of the first and second electrodes is a sacrificial electrode;
    a power source;
    a controller configured to operably couple the power source to the first and second electrodes to create an electric potential between the first and second electrodes so that ions are released from the sacrificial electrode during a brushing session;
    wherein the controller is configured to change a magnitude of the electric potential before the brushing session ends; and
    wherein the controller is configured to change the magnitude in a plurality of discrete steps during at least one part of the brushing session.

2. The oral care device of claim 1, wherein the controller is configured to change the magnitude to zero within a time period which is up to a user brushing period.

3. The oral care device of claim 2, wherein the time period is less than half of the user brushing period.

4. The oral care device of claim 1, wherein both the first and second electrodes are sacrificial electrodes.

5. The oral care device of claim 4, wherein the controller is configured to alternate the electric potential between a positive polarity and a negative polarity during the brushing session.

6. The oral care device of claim 1, wherein at least one of the first electrode and the second electrode comprises zinc.

7. An oral care process comprising:
    generating an electric potential between a first electrode and a second electrode on a head of an oral care device and positioned spaced apart from each other, wherein at least one of the first and second electrodes is a sacrificial electrode, the electric potential resulting in ions being released from the sacrificial electrode during a brushing session;
    changing a magnitude of the electric potential before the brushing session ends; and
    wherein the magnitude is changed in accordance with a polynomial function.

8. The oral care process of claim 7, wherein the magnitude is changed to zero within a time period which is up to a user brushing period.

9. The oral care process of claim 8, wherein the time period is less than half of the user brushing period.

10. The oral care process of claim 7, wherein both the first and second electrodes are sacrificial electrodes.

11. The oral care process of claim 10, further comprising alternating the electric potential between a positive polarity and a negative polarity during the brushing session.

12. The oral care process of claim 7, wherein at least one of the first sacrificial electrode and the second sacrificial electrode comprises zinc.

13. An oral care device comprising:
    a body comprising a head;
    a plurality of teeth cleaning elements extending from the head;
    a first electrode on the head;
    a second electrode on the head and spaced apart from the first electrode, wherein at least one of the first and second electrodes is a sacrificial electrode;
    a power source;
    a controller configured to operably couple the power source to the first and second electrodes to create an electric potential between the first and second electrodes so that ions are released from the sacrificial electrode at a release rate during a brushing session;
    wherein the controller is configured to change a magnitude of the electric potential before the brushing session ends; and
    wherein the release rate is highest at an end of the brushing session.

14. The oral care device of claim 13, wherein the controller is configured to change the magnitude to zero within a time period which is up to a user brushing period.

15. The oral care device of claim 14, wherein the time period is less than half of the user brushing period.

16. The oral care device of claim 13, wherein both the first and second electrodes are sacrificial electrodes.

17. The oral care device of claim 16, wherein the controller is configured to alternate the electric potential between a positive polarity and a negative polarity during the brushing session.

18. The oral care device of claim 13, wherein at least one of the first electrode and the second electrode comprises zinc.

* * * * *